United States Patent [19]
Dobkowski et al.

[11] Patent Number: 6,074,672
[45] Date of Patent: *Jun. 13, 2000

[54] POWDERED COSMETIC COMPOSITIONS CONTAINING SILICONE ELASTOMERS

[75] Inventors: Brian John Dobkowski, Shelton; Alexander Paul Znaiden, Trumbull; Michael Charles Cheney, Fairfield, all of Conn.

[73] Assignee: Chesebrough-Pond's USA Co., Division of Conopco, Inc., Greenwich, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/821,130

[22] Filed: Mar. 20, 1997

Related U.S. Application Data

[60] Provisional application No. 60/020,748, Jun. 28, 1996.

[51] Int. Cl.$^7$ ........................................... A61K 9/14
[52] U.S. Cl. .............................. 424/489; 424/59; 424/65; 424/401
[58] Field of Search .............................. 514/63; 424/489, 424/401, 63, 461, 421

[56] References Cited

U.S. PATENT DOCUMENTS

| | | |
|---|---|---|
| 4,720,353 | 1/1988 | Bell . |
| 4,742,142 | 5/1988 | Shimizu et al. . |
| 4,980,167 | 12/1990 | Harashima et al. . |
| 4,987,169 | 1/1991 | Kuwata et al. . |
| 5,143,722 | 9/1992 | Hollenberg et al. . |
| 5,266,321 | 11/1993 | Shukuzaki et al. . |
| 5,280,019 | 1/1994 | Klimisch . |
| 5,387,417 | 2/1995 | Rentsch . |
| 5,496,544 | 3/1996 | Mellul et al. . |
| 5,545,399 | 8/1996 | Lee et al. ................................. 424/59 |
| 5,582,818 | 12/1996 | Nakanishi et al. ........................ 424/59 |
| 5,654,362 | 8/1997 | Schulz, Jr. et al. . |
| 5,665,393 | 9/1997 | Chen et al. ............................ 424/489 |

FOREIGN PATENT DOCUMENTS

| | | |
|---|---|---|
| 0 388 582 | 1/1990 | European Pat. Off. . |
| 0 709 083 | 5/1996 | European Pat. Off. . |
| 2 688 134 | 9/1993 | France . |
| 04009323 | 1/1992 | Japan . |
| 02304015 | 6/1996 | Japan . |
| 03197413 | 6/1996 | Japan . |
| 95/25499 | 9/1995 | WIPO . |
| 96/018374 WO | 6/1996 | WIPO . |
| 96/018374 | 6/1996 | WIPO . |
| 97/44010 | 11/1997 | WIPO . |

OTHER PUBLICATIONS

GE Silicones Material Safety Data Sheet Jul. 24, 1996.
International Search Report.

*Primary Examiner*—Thurman K. Page
*Assistant Examiner*—William E. Benston, Jr.
*Attorney, Agent, or Firm*—Milton L. Honig

[57] ABSTRACT

A cosmetic powder is provided which includes a crosslinked non-emulsifying siloxane elastomer, a powdered inorganic material and a skin treatment agent. Inclusion of the elastomer allows for the coupling of water as well as water soluble salts into the cosmetic powder.

5 Claims, No Drawings

POWDERED COSMETIC COMPOSITIONS
CONTAINING SILICONE ELASTOMERS

This application is a provisional application Ser. No. 60/020,748 filed Jun. 28, 1996.

BACKGROUND OF THE INVENTION

1. Field of the Invention

The invention concerns cosmetic compositions in powdered form having improved aesthetics through use of special silicone elastomers.

2. The Related Art

Consumers are ever more demanding in the aesthetics delivered by such powdered cosmetics as talcum powder. Much has already been done to improve these products. For instance, Vaseline® Intensive Care® Baby Powder besides talc includes fragrance and the skin conditioning agents of petrolatum and methicone.

The present invention has sought a system which allows inorganic powders to store a high level of hydrophobic and/or hydrophilic liquids. It is of interest to deliver a functional load of lipids, emollients, sunscreens, liquid silicone oils and even water. Particularly attractive would be a capability to incorporate an aqueous emulsion into the powder system. Water soluble compounds could then more readily be incorporated into powders normally unfriendly to such compounds.

Accordingly, it is an object of the present invention to provide a cosmetic powder which delivers improved aesthetics while greatly improving functionality and skinfeel.

Another object of the present invention is to provide a cosmetic powder wherein water can be incorporated and thereby also incorporate water soluble compounds.

These and other objects of the present invention will become more apparent from consideration of the following summary and description.

SUMMARY OF THE INVENTION

A cosmetic powder is provided including:

(i) from 0.1 to 50% of a crosslinked non-emulsifying siloxane elastomer;

(ii) from 1 to 99% of a powdered inorganic material; and (iii) from 0.1 to 20% of a skin treatment agent.

Inorganic powders can now be formulated with high levels of hydrophobic and/or hydrophilic liquids through coupling action of the crosslinked non-emulsifying siloxane elastomer. For instance, water can be incorporated into a hydrophobic liquid coupled with the elastomer which is then loaded onto the inorganic powder. Water soluble actives such as the salts of alpha-hydroxycarboxylic acids can be dissolved in the incorporated water. Thereby normally incompatible water soluble salts can be folded into a hydrophobic system which itself is locked within a cosmetic powder.

DETAILED DESCRIPTION OF THE INVENTION

Now it has been discovered that crosslinked non-emulsifying siloxane elastomers can serve as a coupling vehicle for introducing skin treatment agents into a powder formed mainly of inorganic material.

Crosslinked non-emulsifying siloxane elastomers are a first essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a siloxane polymer with at least two free vinyl groups, reacting with Si—H linkages of a polysiloxane backbone such as a IT molecularly spherical MQ resin. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. Elastomer without cyclomethicone is available from Dow Corning as DC 9506. The commercial products from General Electric and Grant Industries ordinarily are further processed by subjecting them to a high pressure (approximately 5,000 psi) treatment in a Sonolator with recycling in 1 0 to 60 passes. Sonation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.1 to 50%, optimally from 1 to 15%, most preferably from 3 to 10% by weight.

A second essential element of the present invention is that of a powdered inorganic material. The powdered material may be chosen from talc, mica, mineral silicates and mixtures thereof.

Micas useful in the present invention are muscovite, phlogopite, tiotite, sericite, lepidolite, paragonite and artificial or synthetic mica having a fluorine atom substituted for the hydroxyl group of natural mica as well as baked or calcined products thereof. These micas may be used alone or in any mixture thereof.

Mineral silicates useful in the present invention are phyllosilicates and tectosilicates such as pyrophylite, chlorite, antigorite, lizardite, kaolinite, dickite, nacrite, halloysite, montmorillonite, nontronite, saponite, sauconite, and bentonite; natrolites such as natrolite, mesolite, scolecite, and thomsonite; heulandites such as heulandite, stilbite, epistibite; and zeolites such as analcite, harmotone, phillipsite, chabazite and gmelinite. These silicate minerals may be used alone or in combination. The phyllosilicates may have organic cations at the interface of the layers thereof or may be substituted with alkali metal or alkaline earth metal ions. The tectosilicates may include metallic ions in the fine pores thereof.

Amounts of the powdered inorganic material may range from 1 to 99%, preferably from 30 to 85%, optimally from 50 to 75% by weight.

Average particle size of powdered inorganic material according to the present invention will range from 1 to 1,000 microns preferably from 5 to 600 microns, optimally from 80 to 300 microns. The fully formulated cosmetic powder compositions of the present invention will have similar average particle sizes.

A third element of the present invention is that of a skin treatment agent. This agent will be selected from the group consisting of moisturizing conditioners, exfoliants, sunscreens, deodorants and mixtures thereof.

Moisturizing conditioners include humectants, hydrocarbons and oily ester emollients. Humectants are usually polyhydric alcohols. Not only do they moisturize/condition but they function to reduce scaling and stimulate removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. The moisturizing conditioners may also include emollients which can be selected from hydrocarbons or esters. Petrolatum is the most preferred conditioner. Other hydrocarbons that may be employed include mineral oil, polyolefins such as polydecene, and parafins such as isohexadecane (e.g. Permethyl 99® and Permethyl 101®).

Oily ester emollients which moisturize may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.

2. Acetoglyceride esters, such as acetylated monoglycerides.

3. Ethoxylated glycerides, such as ethoxylated glyceryl monostearate.

4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Ether-esters such as fatty acid esters of ethoxylated fatty alcohols.

7. Polyhydric alcohol esters. Ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

8. Wax esters such as beeswax, spermaceti, myristyl myristate, stearyl stearate.

Exfoliants according to the present invention may be selected from alpha-hydroxycarboxylic acids, beta-hydroxycarboxylic acids and salts of these acids. Most preferred are glycolic, lactic and salicylic acids and their ammonium salts.

A wide variety of $C_2$–$C_{30}$ alpha-hydroxycarboxylic acids may be employed. Suitable examples of which include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid Sunscreens may also be used as the skin treatment agent. The sunscreens may be selected from 2-ethylhexyl p-methoxycinnamate, 4,4α-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Deodorants should be capable of killing or hindering the growth of microorganisms that generate malodour or that promote the decomposition of body oils into odiferous fatty acids. Most prominent among organic antimicrobial materials are triclosan, triclorban, chlorhexedine, dibromodicyanobutane, 2-bromo-2-nitropropane-diol-1,3, octenidine salts, alexidine salts, and certain fragrant oils known as deo perfumes (e.g. U.S. Pat. No. 4,278,658 to Hooper et al.). Inorganic antimicrobial materials may also serve as deodorant actives. These include zinc oxide, zinc hydroxide, zinc carbonate, zinc phenolsulfonate, magnesium oxide, magnesium hydroxide, magnesium carbonate, lanthanum oxide, lanthanum hydroxide, lanthanum carbonate and combinations thereof.

Deodorancy may also be achieved from astringent salts such as those of aluminum, zirconium, zinc and mixtures thereof. Salts useful as astringents or as components of astringent complexes include aluminum halides, aluminum hydroxyhalides, zirconyl oxyhalides, zirconyl hydroxyhalides and mixtures of these salt materials.

Amounts of the skin treatment agent may range from 0.1 to 20%, preferably from 0.5 to 15%, optimally from 1 to 10% by weight. Compositions of this invention may include volatile and nonvolatile silicones other than the crosslinked elastomers.

The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from 0.1 to 8 centistokes. Examples of silicone oils useful in the present invention include: Dow Corning 344, Dow Corning 345 and Dow Corning 244 (manufactured by the Dow Corning Corporation); Silicone 7207 and Silicone 7158 (manufactured by the Union Carbide Corporation); SF1202 (manufactured by General Electric).

Non-volatile polyorganosiloxanes may be fluids selected from polyalkyl siloxane, polyalkylaryl siloxane or polyether siloxane copolymers. The non-volatile polyalkyl siloxanes that may be used include, for example, polydimethyl siloxanes with viscosities ranging from about 5 to 100,000 centistokes at 25° C. These siloxanes are available from the General Electric Company as the Vicasil series and from Dow Corning as the Dow Corning 200 series. The non-volatile polyalkylaryl siloxanes may include, for example, polymethylphenylsiloxanes having viscosities of from 15 to 65 centistokes at 25° C. These siloxanes are available from the General Electric Company as SF 1075 methyl phenyl fluid or from Dow Corning as 556 Cosmetic Grade Fluid. The non-volatile polyether siloxane copolymer may include, for example, a dimethyl polyoxyalkylene ether copolymer fluid having a nominal viscosity of about 1200 to 1500 centistokes at 25° C. The copolymer is available from the General Electric Company as SF-1066 organosilicone surfactant. Preferred compounds of this type are polysiloxane ethylene glycol ether copolymers.

Cosmetic powders of the present invention are prepared in the following manner. An aqueous emulsion is formed from a combination of water and a volatile oil siloxane elastomer blend. One or more skin treatment agents are emulsified into the emulsion. It is most preferable that a water-in-oil type emulsion be formed. When the aqueous phase is internal, the phase will later be protected from evaporation and thereby entrapped with the dried residue of the crosslinked elastomer. Volatile oils such as cyclomethicone and $C_5$–$C_{40}$ hydrocarbons are useful as the evaporative component. Relative weight ratios of the water and oil phases may range from 20:1 to 1:2, preferably from 10:1 to 1:1, optimally from 6:1 to 2:1. Subsequent to emulsion formation, volatile oils are stripped by evaporation. The resultant dried blend is then mixed with powdered inorganic material such as talc. The resultant powder is then subjected to high shear mixing in an Osterizer or equivalent apparatus.

The following examples will more fully illustrate the embodiments of this invention. All parts, percentages and proportions referred to herein and in the appended claims are by weight unless otherwise indicated.

EXAMPLE 1

This Example illustrates a typical talcum powder product achievable by the present invention. A water-in-oil emulsion is formed by blending the potassium lactate solution into elastomer dispersed within cyclomethicone (with petrolatum and emulsifier). The resultant blend (see Table I) is then poured into and mixed with powdered talc in a ratio of 1:10 to form a talcum powder.

TABLE I

| COMPONENT | WEIGHT % |
|---|---|
| Gransil SR-CYC ® | 22.5 |
| DC 344 ® (Cyclomethicone) | 54 |
| Petrolatum | 11 |
| Potassium Lactate (50% Water) | 7 |
| ABIL EM90 ® (Silicone copolyol) | 0.5 |

EXAMPLE 2

This Example provides a series of comparative experiments to demonstrate the unique character of the silicone elastomer in contrast to other thickening silicone materials. Table II lists the formulations and Table III describes the physical properties of the resultant compositions.

TABLE II

| TRADE NAME | CTFA NAME | FORMULATIONS (WEIGHT %) | | | | | |
|---|---|---|---|---|---|---|---|
| | | A | B | C | D | E | F |
| PJ 2.5 hard | Petrolatum | 0.3 | 0.3 | 0.3 | 0.3 | 0.3 | 0.3 |
| Purac BFP39 | Potassium Lactate | 5 | 5 | 5 | 5 | 5 | 5 |
| Permethyl 99a | C12–14 isoparafin | 0.5 | 0.5 | 0.5 | 0.5 | 0.5 | 0.5 |
| Abil EM90 | Cetyl dimethicone-copolyol | 0.2 | 0.2 | 0.2 | 0.2 | 0.2 | 0.2 |
| Talc | Talc | 54 | 54 | 54 | 54 | 54 | 54 |
| DC 9506 | Silicone Elastomer | 40 | | | | | |
| DC 593 | Trimethylsiloxy-silicate | | 40 | | | | |
| Abil 9801 | Cetyl-Dimethicone | | | 40 | | | |
| Abil 9800 | Stearyl Dimethicone | | | | 40 | | |
| GE SE30 | Dimethicone | | | | | 40 | |
| Dow 556 | Phenyl Trimethicone | | | | | | 40 |

TABLE III

| | FORMULATIONS | | | | | |
|---|---|---|---|---|---|---|
| | A | B | C | D | E | F |
| Results: | Flowable powder | Very thick pourable | Pourable Liquid | Solid non-powder | Slightly pourable very thick liquid | Pourable liquid |

Based upon the results in Table 111, only the silicone elastomer (Dow Corning 9506) provided a composition that was a flowable powder. All other formulations were not in powder form.

The foregoing description and Examples illustrate select embodiments of the present invention. In light thereof, various modifications will be suggested to one skilled in the art, all of which are within the spirit and purview of this invention.

What is claimed is:

1. A cosmetic powder comprising:
   (i) from 0.1 to 50% of a crosslinked non-emulsifying siloxane elastomer;
   (ii) from 1 to 99% of a powdered inorganic material; and
   (iii) from 0.1 to 20% of a skin treatment agent.

2. The powder according to claim 1 wherein the skin treatment agent is selected from the group consisting of moisturizing conditioners, exfoliants, sunscreens, deodorants and mixtures thereof.

3. The powder according to claim 1 wherein the skin treatment agent is selected from the group consisting of an alpha-hydroxycarboxylic acid, beta-hydroxycarboxylic acid and salts thereof.

4. The powder according to claim 1 wherein the crosslinked non-emulsifying siloxane elastomer is formed from a divinyl compound reacted with Si—H linkages of a polysiloxane.

5. The powder according to claim 1 wherein the inorganic material is talc.

* * * * *